(12) United States Patent
Zemenchik et al.

(10) Patent No.: US 11,064,646 B2
(45) Date of Patent: Jul. 20, 2021

(54) SYSTEM FOR TREATMENT OF AN AGRICULTURAL FIELD WITH REAL TIME SENSING OF SOIL VARIABILITY AND/OR CLOD STABILITY

(71) Applicant: CNH Industrial America LLC, New Holland, PA (US)

(72) Inventors: Robert A. Zemenchik, Kenosha, WI (US); Matt Huenemann, Racine, WI (US)

(73) Assignee: CNH Industrial America LLC, New Holland, PA (US)

( * ) Notice: Subject to any disclaimer, the term of this patent is extended or adjusted under 35 U.S.C. 154(b) by 78 days.

(21) Appl. No.: 16/148,112

(22) Filed: Oct. 1, 2018

(65) Prior Publication Data
US 2019/0141880 A1 May 16, 2019

Related U.S. Application Data

(60) Provisional application No. 62/585,392, filed on Nov. 13, 2017.

(51) Int. Cl.
*A01B 79/00* (2006.01)
*A01B 63/32* (2006.01)
(Continued)

(52) U.S. Cl.
CPC ............ *A01B 79/005* (2013.01); *A01B 63/32* (2013.01); *A01C 5/064* (2013.01); *A01C 7/203* (2013.01);
(Continued)

(58) Field of Classification Search
CPC ... A01B 79/005; A01B 63/32; A01B 63/1115; A01C 5/064; A01C 7/203; A01C 21/007; G01N 33/24; G01N 2033/245
See application file for complete search history.

(56) References Cited

U.S. PATENT DOCUMENTS

| | | | |
|---|---|---|---|
| 4,409,910 A | | 10/1983 | Hoyle et al. |
| 4,835,691 A | * | 5/1989 | Rotem ................. A01B 69/004 |
| | | | 172/6 |

(Continued)

FOREIGN PATENT DOCUMENTS

WO WO-2017049186 A1 * 3/2017 ............. A01B 63/24

OTHER PUBLICATIONS

Michael L. Oleze, James M. Sabatier, and Richard Raspet, "Roughness Measurements of Soil Surfaces by Acoustic Backscatter", Journal, Jan.-Feb. 2003, 10 pages, Soil Science Society of America Journal.

*Primary Examiner* — Tara Mayo-Pinnock
(74) *Attorney, Agent, or Firm* — Rebecca L. Henkel; Rickard K. DeMille

(57) ABSTRACT

The invention provides a system for sensing soil characteristics of an agricultural field, including soil variability and/or clod stability, in real time to allow rapid adjustment of an implement while traversing the field. The implement could be a planter, a fertilizer applicator or a tillage implement treating the field with ground engaging tools. The system can sense the soil characteristics, for example, by continuously transmitting acoustic energy to the field and sensing sound energy scattered back. This, in turn, can allow a continuously updated estimation of the field, such as in terms of clod size. Adjustment of the implement can include changing its speed and/or application of a seedbed attachment, such as changing a depth of the ground engaging tool.

15 Claims, 5 Drawing Sheets

(51) Int. Cl.
*A01C 21/00* (2006.01)
*A01C 5/06* (2006.01)
*G01N 33/24* (2006.01)
*A01C 7/20* (2006.01)
*A01B 63/111* (2006.01)

(52) U.S. Cl.
CPC ........... *A01C 21/007* (2013.01); *G01N 33/24* (2013.01); *A01B 63/1115* (2013.01); *G01N 2033/245* (2013.01)

(56) References Cited

U.S. PATENT DOCUMENTS

| | | | |
|---|---|---|---|
| 4,914,593 A * | 4/1990 | Middleton | E02F 3/847 172/4 |
| 4,918,608 A * | 4/1990 | Middleton | E02F 3/847 172/4 |
| 4,924,374 A * | 5/1990 | Middleton | E02F 3/847 172/4.5 |
| 4,982,086 A | 1/1991 | Withjack | |
| 4,987,841 A | 1/1991 | Rawson et al. | |
| 5,044,756 A | 9/1991 | Gaultney et al. | |
| 5,184,293 A * | 2/1993 | Middleton | E02F 3/847 172/4.5 |
| 5,235,511 A * | 8/1993 | Middleton | E02F 9/2045 172/4 |
| 5,355,815 A | 10/1994 | Monson | |
| 5,473,999 A | 12/1995 | Rawson et al. | |
| 5,884,224 A * | 3/1999 | McNabb | A01G 7/00 700/284 |
| 5,956,255 A | 9/1999 | Flamme | |
| 6,152,238 A * | 11/2000 | Ferrell | E02F 3/847 172/2 |
| 6,199,000 B1 * | 3/2001 | Keller | A01B 79/005 701/50 |
| 6,898,501 B2 * | 5/2005 | Schubert | B60G 17/0165 180/89.12 |
| 6,937,939 B1 | 8/2005 | Shibusawa et al. | |
| 8,022,353 B2 | 9/2011 | Leuenberger et al. | |
| 8,078,367 B2 | 12/2011 | Sauder et al. | |
| 8,359,141 B1 * | 1/2013 | Lange | A01B 69/008 172/2 |
| 8,453,754 B2 * | 6/2013 | Beaujot | A01B 63/16 172/2 |
| 8,849,523 B1 * | 9/2014 | Chan | G01S 13/89 701/50 |
| 8,862,339 B2 | 10/2014 | Henry et al. | |
| 8,950,260 B2 | 2/2015 | Gelinske et al. | |
| 9,265,192 B2 | 2/2016 | Chan et al. | |
| 9,651,536 B1 | 5/2017 | Lund et al. | |
| 2011/0184551 A1 * | 7/2011 | Kowalchuk | A01C 7/105 700/219 |
| 2012/0042813 A1 * | 2/2012 | Liu | A01C 7/105 111/149 |
| 2012/0046838 A1 * | 2/2012 | Landphair | A01B 79/005 701/50 |
| 2015/0305226 A1 * | 10/2015 | Zemenchik | A01C 21/007 701/50 |
| 2015/0305228 A1 | 10/2015 | Zemenchik | |
| 2016/0355187 A1 * | 12/2016 | Nothdurft | B60W 30/18172 |
| 2016/0360692 A1 | 12/2016 | McCloskey | |
| 2017/0006758 A1 * | 1/2017 | Dienst | A01B 63/22 |
| 2017/0094894 A1 | 4/2017 | Heim et al. | |
| 2018/0014450 A1 * | 1/2018 | Dienst | A01C 21/002 |
| 2018/0124992 A1 * | 5/2018 | Koch | A01B 79/005 |

\* cited by examiner

SYSTEM FOR TREATMENT OF AN AGRICULTURAL FIELD WITH REAL TIME SENSING OF SOIL VARIABILITY AND/OR CLOD STABILITY

CROSS-REFERENCE TO RELATED APPLICATION(S)

This application claims priority to U.S. Provisional Patent Application No. 62/585,392, entitled "Sensor for Soil Roughness Data Streaming to Govern Planter Speed and Provide Seedbed Amendment," filed Nov. 13, 2017, which is herein incorporated by reference.

FIELD OF THE INVENTION

This invention relates generally to agricultural implements, and in particular, to the use of one or more sensors on an implement, such as a planter, fertilizer applicator, or tillage implement (e.g. a seedbed preparation tool) for sensing soil roughness in which the speed of the implement or the application of a seedbed attachment may be provided in response thereto.

BACKGROUND OF THE INVENTION

Increased planting speeds and advances in telematics systems require the development of agronomic data-rich innovations to deliver new customer value and grow competitiveness. New planter speeds of up to 10 miles-per-hour (mph) require new sensor-based data streams to govern planter ground speed, row unit down pressure, and other features to improve the seed-soil environment for greater crop yield potential. Heretofore, manufactures are selling planters capable of higher speeds. However, such high speed planters utilize very limited data with respect to the soil-seed environment. Consequently, it is highly desirable to provide on-the-go technologies that measure, report and improve automatic seedbed or planter-related innovations for operations ahead of planting in order to improve machine performance, stand quality, and plant vigor with greater yield potential with these technologies.

SUMMARY OF THE INVENTION

The invention provides a system for sensing soil characteristics of an agricultural field, including soil variability and/or clod stability, in real time to allow rapid adjustment of an implement while traversing the field. The implement could be a planter, a fertilizer applicator or a tillage implement treating the field with ground engaging tools. The system can sense the soil characteristics, for example, by continuously transmitting acoustic energy to the field and sensing sound energy scattered back. This, in turn, can allow a continuously updated estimation of the field, such as in terms of clod size. Adjustment of the implement can include changing its speed and/or application of a seedbed attachment, such as changing a depth of the ground engaging tool.

As is known, soil variability (moisture, texture, organic matter) in the field contributes to variability in seedbed quality at planting. Clod stability in the field is a function of soil texture, moisture and organic matter, By experience, farmers attempt to wait until the soil moisture is ideal for maximum friability on the majority of the soil in the field. For example, if the soil is too dry, soil cohesion will keep clod size too big. If the soil is too wet cohesion will cause slabbing and adhesion will cause operational sticking. Knowing that soil texture and organic matter are subject to wide ranging special variability on the landscape, the farmer is forced to manage-on-the-mean, satisfied with the result from the majority of his cultivation operations, but wholly dissatisfied with the remainder. In cultivated regions of the U.S. Midwest, it would not be unexpected to see 10-20% of field acres planted either late, or in less than ideal condition due to these factors. It can be appreciated that if an improvement in net effective stand could be obtained, the production per acre could increase dramatically.

Recently, mounted rolling reels for field cultivators, disk harrows and vertical tillage tools have been developed. Such rolling reels can improve net effective stands by as much as 9%. Their cutting power increases with speed or down-pressure, which could be automated. Moreover, machine ground speed could also be increased in such areas. In high organic matter soils, the opposite is true and standard pressure and speed is recommended. However, even after such attachments go over the field, some areas could still benefit with further management. As such, a proliferation of planter attachments and down force technology has occurred over the last few years for planters. This is problematic as planters are forced to become tillage tools, seed delivery machines, fertilizer applicators, etc.

Specifically then, one aspect of the present invention can provide a system for treatment of an agricultural field, including: a sensor for connecting to an agricultural implement, the sensor sensing a soil variability and/or a clod stability of soil in the field as the implement traverses the field and providing the same as a sensed signal; and a processor operatively connected to the sensor, the processor executing a program stored in non-transient medium to cause a change to a speed of the implement and/or an application of a seedbed attachment provided in response to the sensed signal.

Another aspect of the present invention can provide an agricultural implement including: a frame supported by wheels; a ground engaging tool supported by the frame; a sensor operatively connected to the implement, the sensor sensing a soil variability and/or a clod stability of soil in a field as the implement traverses the field and providing the same as a sensed signal; and a processor operatively connected to the sensor, the processor executing a program stored in non-transient medium to cause a change to a speed of the implement and/or an application of the ground engaging tool provided in response to the sensed signal.

Another aspect of the present invention can provide a method for treatment of an agricultural field, including: sensing a soil variability and/or a clod stability of soil in a field from a sensor operatively connected to an agricultural implement while the implement is traversing the field; providing the sensed soil variability and/or clod stability from the sensor as a sensed signal to a processor; and processing a value in response to the sensed signal to change a speed of the implement and/or an application of a seedbed attachment.

Other aspects, objects, features, and advantages of the invention will become apparent to those skilled in the art from the following detailed description and accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

DETAILED DESCRIPTION OF THE DRAWINGS

Figure 1:
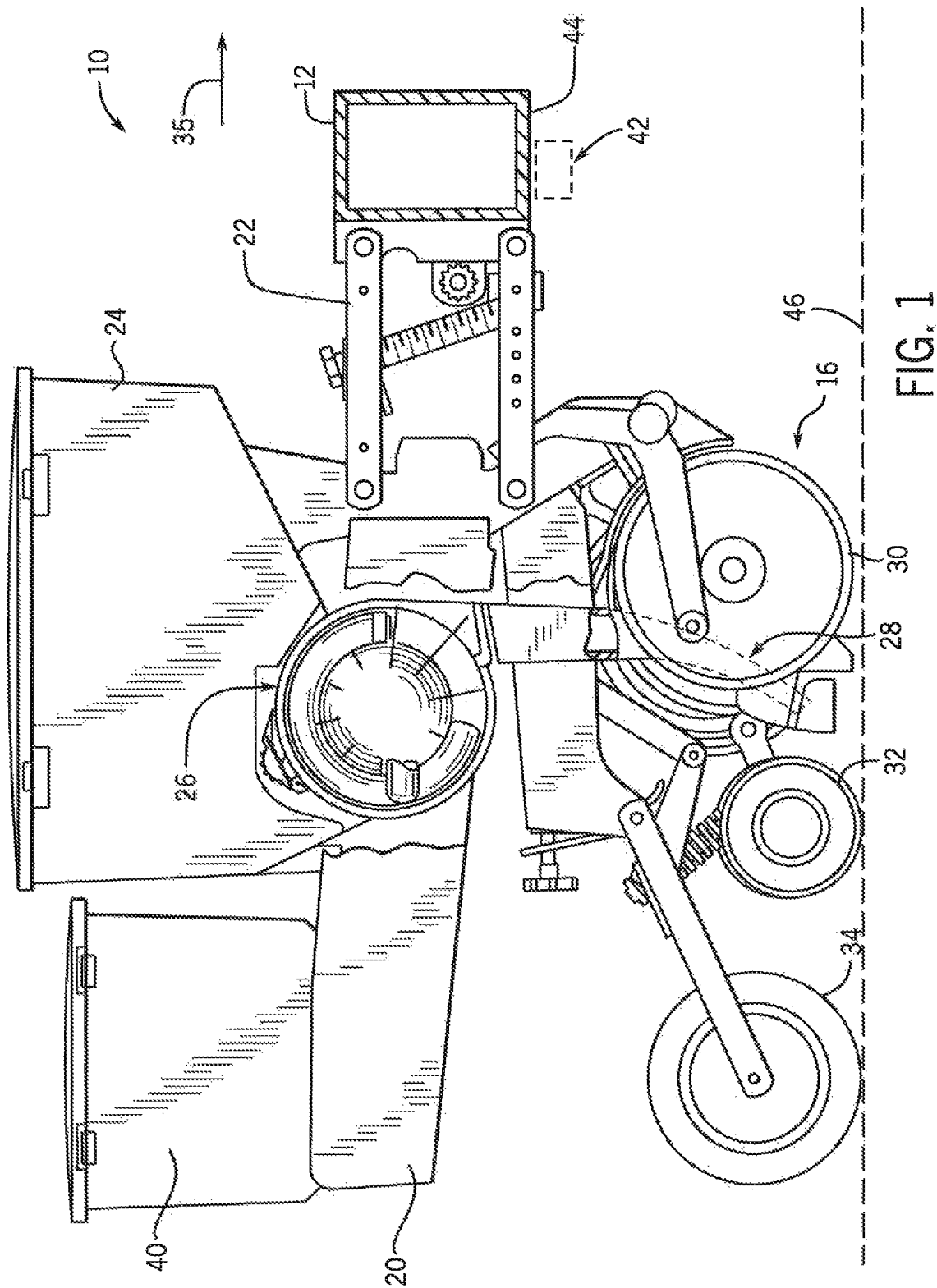
FIG. 1 is side elevational view of a row unit of a planter incorporating a sensor in accordance with present invention.

Referring to FIG. 1, a planter incorporating a sensor array in accordance with the present invention, is generally designated by the reference numeral 10. As is conventional, planter 10 includes a tool bar 12 as part of a planter frame. Mounted to the tool bar are multiple planting row units 16. Row units 16 are typically identical for a given planter but there may be differences. Each row unit 16 is provided with a central frame member 20 connected to a parallelogram linkage 22 for mounting the row unit 16 to the tool bar 12 for up and down relative movement between the unit 16 and tool bar 12 in a known manner. Seed is stored in seed hopper 24 at the row unit 16 or may be centrally stored in a bulk storage container that and pneumatically conveyed to each row unit. Regardless of the type of seed storage, at each row unit 16, the seed is provided to a seed meter 26. Seed meter 26 may be of the type that uses a vacuum disk or other metering member that can cingulate seed as are well known to meter the seed. Other types of meters can be used as well. From the seed meter 26 the seed is carried by a delivery system 28 into a planting furrow, or trench, formed in the soil by furrow openers 30. Gauge wheels 32 control the depth of the furrow. Closing wheels 34 close the furrow over the seed. The toolbar and row unit are designed to be moved over the ground in a forward working direction identified by the arrow 35.

The row unit 16 may also include chemical hopper 40, a row cleaner attachment (not shown) and a down force generator (not shown). The row unit 16 is shown as an example of the environment in which sensor array 42 of the present invention may be used. However, sensor array 42 can be used in any of a variety of planting machine types such as, but not limited to, row crop planters, grain drills, air seeders, etc.

Figure 4:
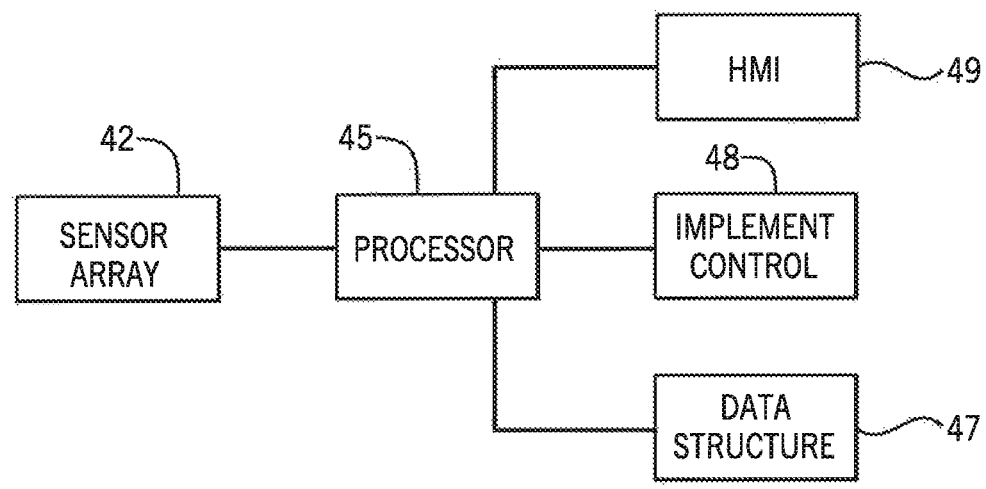
FIG. 4 is a schematic view of a system with a sensor of the present invention.

By way of example, sensor array, for example, an acoustic backscatter (AB) sensor array, 42 may be mounted to the underside 44 of tool bar 12. In operation, as planter 10 traverses field 46, sensor array 42 transmits short pulses of acoustic energy directed toward field 46. As the sound pulse dissipates from sensor array 42, it engages the soil in field 46, thereby causing the sound energy to scatter. A portion of the sound energy is reflected back towards sensor array 42, which also acts as a sound receptor. With knowledge of the speed of sound in the soil, the scattering strength of the soil and the materials therein and the sound propagation characteristics, a relationship may be developed between the intensity of the received echoes and the characteristics of the soil. The magnitude of the backscattered signal can be related to the soil variability and the clod stability in field 46. More specifically, with additional reference to FIG. 4, the backscattered signal may be provided to a corresponding processor 45 which delivers a micro-profileometer of soil aggregate size distribution. The degree of resolution will allow detailed seedbed assessment to 2", seedbed soil porosity and clod size distribution displayed as histogram. This can be directly used to govern planter operating speeds since it is more than a topography map; it is an assessment of seedbed quality. Intervening measures such as supplemental soil preconditioning may be developed in conjunction with this data.

In one aspect, processor 45 can execute a program stored in non-transient medium, such as a data structure 47, to update an implement control 48, such as a control module controlling a speed of the implement and/or an application of a seedbed attachment, in response to the sensing. The implement control 48 could comprise an interface with the engine and/or a cylinder or other mechanical element controlling up and down relative movement between the unit 16 and tool bar 12 and/or the gauge wheels 32. Accordingly, data structure 47 can contain an updateable program for execution by the processor 45 while conducting field operations. In addition, data structure 47 can contain modifiable parameters guiding treatment of the field. Such parameters can include, for example, thresholds for soil characteristics relating to soil variability and/or clod stability of soil in the field, such as minimum and/or maximum estimations for clod sizes, before providing corresponding updates to the implement control 48, such as with respect to speeds and/or ground engaging depths. For example, based on sensed soil characteristics, processor 45 could continuously estimate soil clod/residue sizes with corresponding responses thereto based on threshold, such as: an estimated clod size threshold of 2" or less resulting in a speed of 10 mph and/or ground engaging depth of 2"; an estimated clod size threshold between 2" to 3" resulting in a speed of 8 mph and/or ground engaging depth of 3"; an estimated clod size threshold between 3" to 4" resulting in a speed of 6 mph and/or ground engaging depth of 4"; and so forth. In addition, the processor 45 can operatively connect to Human Machine Interface (HMI) 49, which is preferably disposed in operator cab associated with the planter. The HMI 49 can provide an interface for displaying characteristics of the field, including the histogram, displaying the aforementioned parameters stored of the data structure 47, and/or receiving updates for such parameters, among other things.

Figure 2:
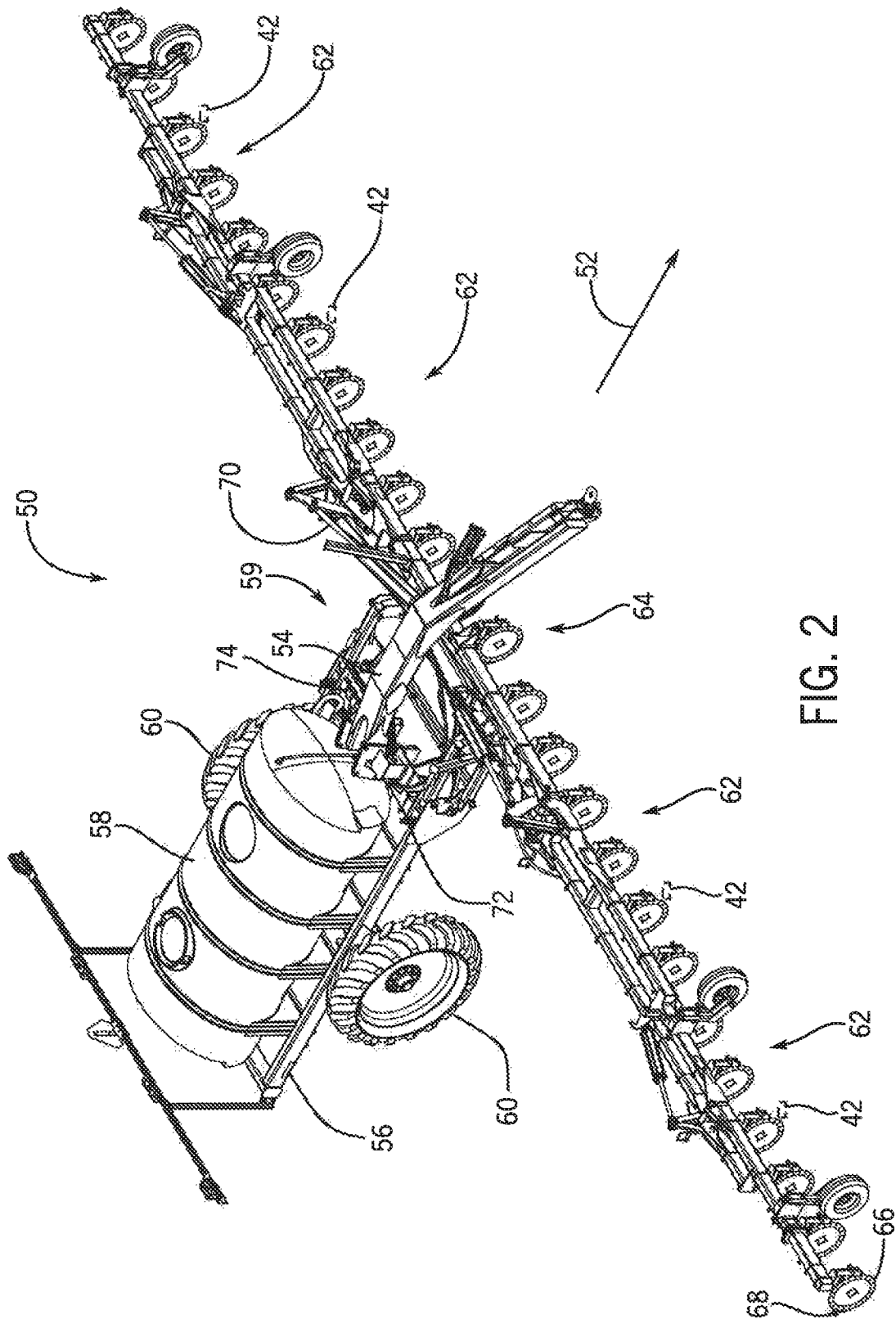
FIG. 2 is an isometric view of a fertilizer applicator incorporating the sensor of the present invention.

Referring to FIG. 2, fertilizer applicator 50 has a flow controller mounted remotely from a pump. In the illustrated embodiment, the applicator 50 is configured to be towed along a direction of travel 52 by a work vehicle, such as a tractor or other prime mover. The work vehicle may be coupled to the applicator 50 by a hitch assembly 54, such as the illustrated "goose neck" pull frame. Hitch assembly 54 is coupled to a main frame 56 of the applicator 50 to facilitate towing of the applicator 50 in the direction of travel 52. In the illustrated embodiment, the main frame 56 supports a storage tank 58 configured to house a flowable agricultural product, such as liquid fertilizer. The storage tank 58 may be a substantially cylindrical vessel. A pair of wheels 60 coupled to the main frame 56 is configured to support the weight of the frame 56, the storage tank 58, and the flowable agricultural product, thereby enabling the applicator 50 to be towed across the field.

The applicator 50 is configured to transfer the flowable agricultural product from the storage tank 58 to multiple row units 62 with coulters of a tool bar assembly 64. Each row unit 62 includes a ground engaging tool 66 configured to break the soil, thereby excavating a trench into the soil. An injection nozzle 68 or knife (e.g., positioned behind the ground engaging tool) is configured to deposit flowable agricultural product from the storage tank 58 into the trench formed by the ground engaging tool 66. In certain embodiments, the penetration depth of the ground engaging tools 66 is adjustable to facilitate deposition of the agricultural product at a desired depth beneath the soil surface. Accordingly, a flowable agricultural product, such as liquid fertilizer, may be distributed throughout a field, either before or after planting, to facilitate enhanced crop development.

While the illustrated applicator 50 includes 25 row units 62, it should be appreciated that alternative applicators may include more or fewer row units 62. In addition, the number of row units and the spacing between row units may be particularly selected to correspond to the arrangement of row units on respective seeding or planting applicators. For example, the applicator 50 may include 25 row units 62 spaced 30 inches from one another. Accordingly, as the applicator 50 is towed across a field, the row units 62 deposit fertilizer in rows having 30-inch spacing. After the fertilizer is applied, a seeding or planting applicator (e.g., having row units spaced 30 inches from one another) may deposit seeds between the rows of fertilizer (e.g., at the approximate midpoint between rows), thereby facilitating enhanced crop development. In addition, the applicator 50 may be utilized to apply fertilizer to previously planted seeds (e.g., via injecting fertilizer between rows of previously planted seeds).

One or more controls of a control system 59 are configured to control the deposition of the fertilizer by the row units 62. In some embodiments, actuators 70 may adjust the height of at least some of the row units 62 of the tool bar assembly 64 (e.g., to change the number of rows to be fertilized). The actuators 70 may adjust the height of the row units 62 using hydraulic pistons, pneumatic pistons, and/or electric motors. An actuator controller 72 (e.g., hydraulic controller) is mounted on the agricultural applicator 50 to control the actuators 70. In some embodiments, a hydraulic controller is fluidly coupled to each actuator 70, and is configured to control the height of at least some of the row units 62 relative to the field. A flow controller 74 is mounted on the agricultural applicator 50, and is configured to direct the fertilizer through conduits to the injection nozzles 68 to deposit the fertilizer into soil.

For seedbed soil micro-profile assessment ahead of the inter-rows between ground engaging tools 66 on the applicator 50 for pre-plant soil preconditioning, sensor arrays 42 may be connected to tool bar assembly 64. Sensor array 42 deploys a high frequency acoustic signal. As heretofore described, a portion of the sound energy is reflected back towards sensor array 42, which also acts as a sound receptor. The reflected signal is transmitted to processor 45. With knowledge of the speed of sound in the soil, the scattering strength of the soil and the materials therein and the sound propagation characteristics, the magnitude of the backscattered signal can be utilized to determine the need for further tillage and conditioning if excessive cloddiness. Pneumatic soil conditioning baskets may be applied as needed. The data stream may be used to drive hybrid selection, seeding rate, and tillage conditioning.

In one aspect, processor 45 can execute a program stored in data structure 47 to update implement control 48 comprising actuator controller 72 in response to the sensing. This can control the height of individual ones of the row units 62. In addition, processor 45 can execute the program to update a speed in which the applicator 50 is towed in response to the sensing.

Figure 3:
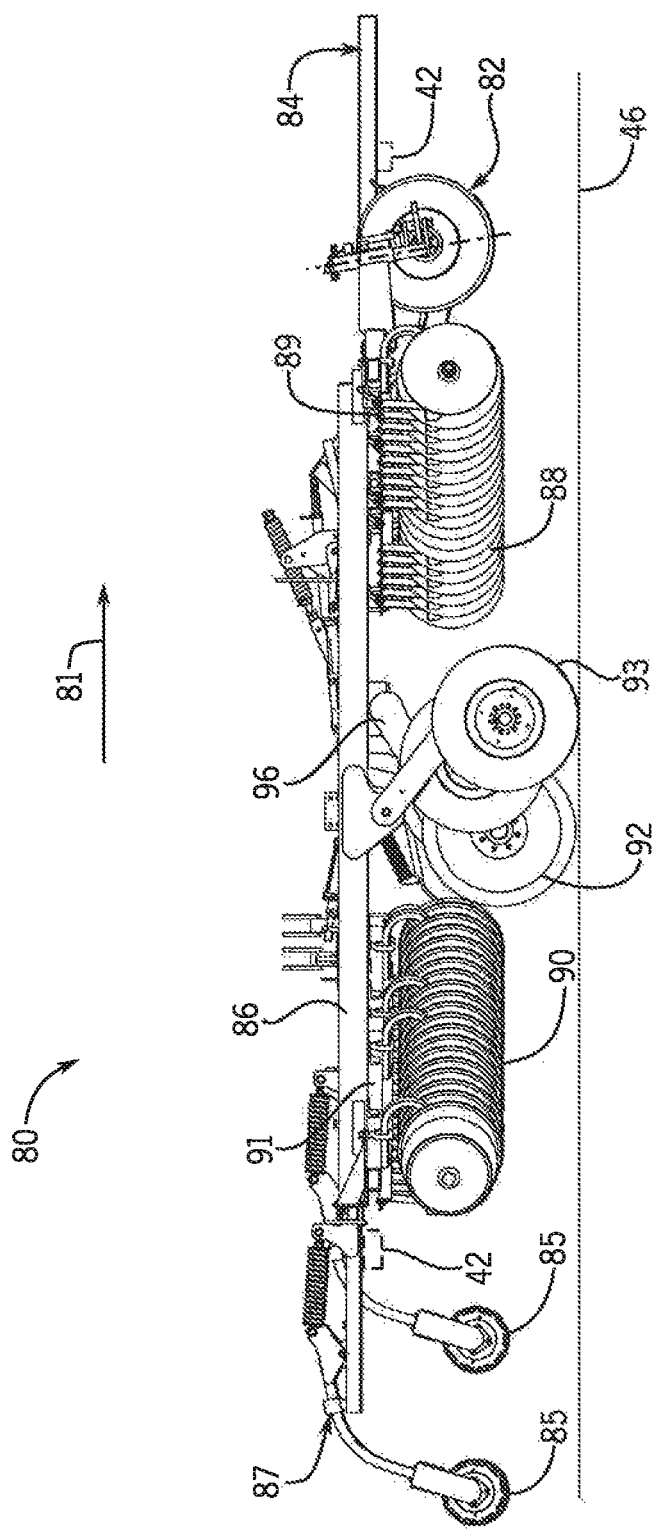
FIG. 3 is an isometric view of a tillage implement incorporating the sensor of the present invention.

Referring to FIG. 3, an exemplary embodiment of a towable agricultural implement, according to the invention, in the form of a tandem disk 80, including a pair of left and right remotely adjustable stabilizer wheel arrangements 82, configured to be towed along a direction of travel 81. The disk 80 includes a hitch 84, which has a distal end that is adapted for operative attachment to a towing vehicle, such as a tractor. The disk 80 has a frame 86 that includes a pair of left and right floating wings connected to a central main section of the frame 86 by a plurality of hinged joints. The disk 80 also includes segmented front and rear tillage tools, in the form of front and rear disk gangs or tillage tools 88 and 90, that are operatively joined to the frame 86 by front and rear segmented tool bars 89 and 91 respectively. The tool bars 89 and 91 and tillage tools 88 and 90 are segmented and attached to the main frame 86 and wing frames in a manner that allows the wing frames and the segments of the front and rear tillage tools 88 and 90 to be folded above the center section of the frame 86, to thereby narrow the disk 80 for transport on public roadways. A pair of rolling reels 85 is interconnected to a trailing end 87 of main frame 86.

The disk 80 is supported above field 46 by two pairs of tandem support wheels 92 and right and left pairs of wing frame support wheels 93. The pairs of support and wing frame wheels 92 and 93, respectively, are all operatively attached to the frame 86 by a common depth control arrangement 96, in a manner that allows the depth control arrangement 96 to set and maintain a depth of penetration of the tillage tools 88 and 90 below in field 46, in the manner known in the art.

It is contemplated to mount sensor arrays 42 upstream of wheel arrangement 82 and upstream of rolling reels 85. The reels 85 are configured as crumblers that have spirally arranged blades or bars as formed, twisted shapes that engage the ground to reduce clod sizes and residue. In operation, sensor arrays 42 deploys a high frequency acoustic signal. As heretofore described, a portion of the sound energy is reflected back towards sensor array 42, which also acts as a sound receptor. The reflected signal is transmitted to processor 45. With knowledge of the speed of sound in the soil, the scattering strength of the soil and the materials therein and the sound propagation characteristics, the magnitude of the backscattered signal can be utilized by the processor 45 to automatically adjust the cutting power of the rolling reels 85 as the speed of disk 80 traversing field 46 or the down-pressure on front and rear tillage tools 88 and 90 is varied.

In one aspect, processor 45 can execute a program stored in data structure 47 to update implement control 48 comprising the depth control arrangement 96 in response to the sensing. This can control depth of penetration of the tillage tools 88 and 90. Processor 45 can also execute the program to control down pressure with respect to reels 85 in response to the sensing. In addition, processor 45 can execute the program to update a speed in which the tandem disk 80 is towed in response to the sensing.

Figure 5:
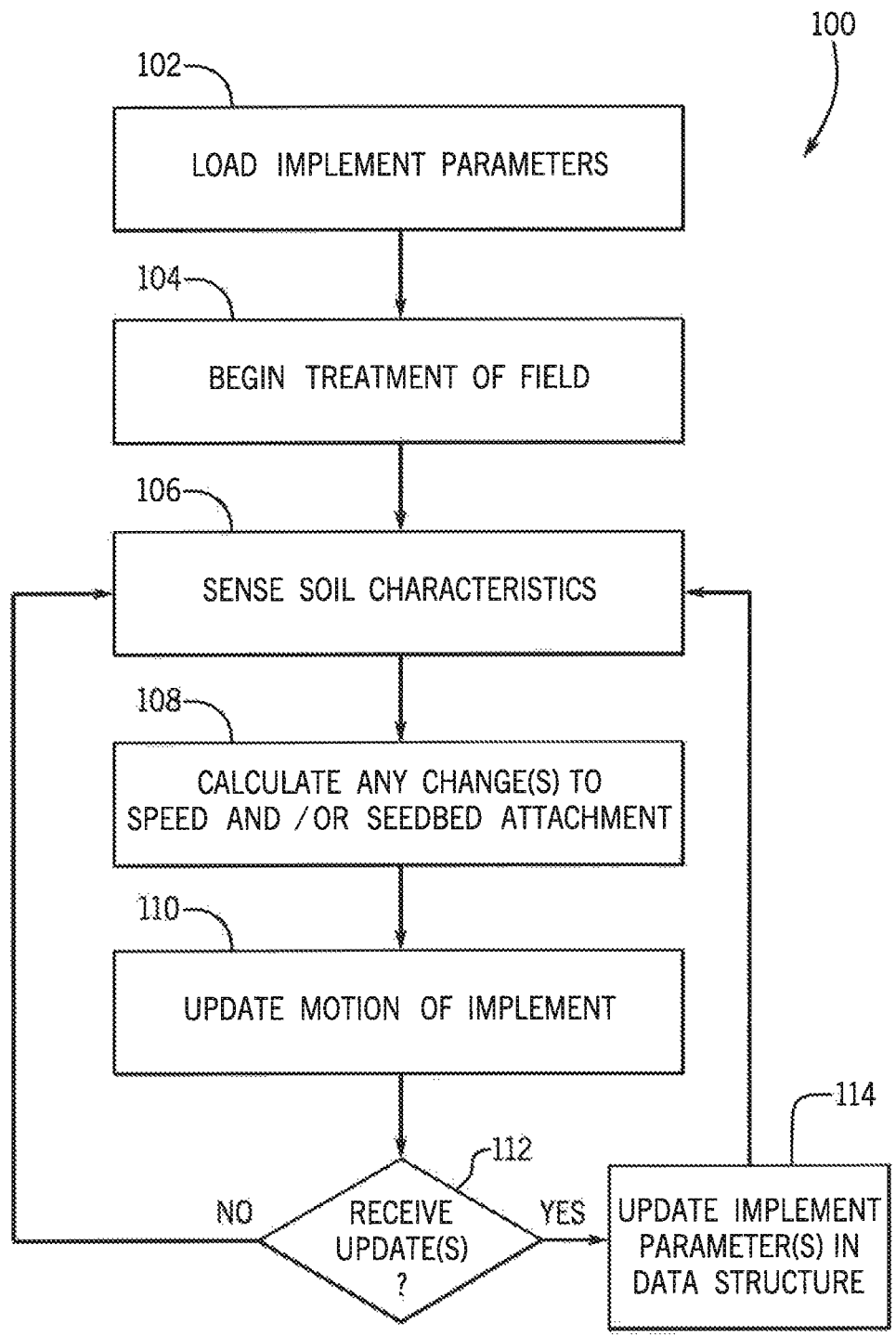
FIG. 5 is a flow chart illustrating operation of a system for treatment of an agricultural field in accordance with present invention.

Referring now to FIG. 5, in accordance with aspect of the invention, a process 100 illustrates exemplar operation of a system for treatment of an agricultural field. The process 100, which may be governed by the program in the data structure 47 and executed by the processor 45, can begin at step 102 in which parameters are loaded from the data structure 47. The parameters can define thresholds, such as clod/residue sizes, in which the treatment is carried out, such as speeds and ground engaging depths. Next, at step 104, treatment of the field can begin as the implement traverses the field while the processor 45 executes to control the speed and engagement of ground engaging tools at given depths and pressures. Then, at step 106, as the implement traverses the field, the system can sense soil variability and/or clod stability of soil in the field from sensor array 42.

Next, at step 108, processor 45 can execute to calculate any necessary changes to speed and/or application of a seedbed attachment based soil characteristics sensed from sensor array 42 and thresholds stored as parameters in data structure 47. In one aspect, the processor 45 can quantify sensed soil variability and/or clod stability and compare such quantified values to parameters of the data structure 47 defining thresholds. Then, at step 110, processor 45 can execute to update motion of the implement through the implement control 48 based on meeting such thresholds, such as updating a speed of the implement and/or ground engaging depth of the implement based on encounter larger or smaller estimated clod sizes, while traversing the field.

Then, at decision step 112, processor 45 can determine whether input is received, such as from an operator via the HMI 49. The input could be, for example, modification of a parameter defining an estimated clod size in which a speed or ground engaging depth might change, and/or modifications of parameters defining the speeds and/or ground engaging depths themselves. If an input is received ("Yes"), processor 45 can update parameter of data structure 47 at step 114 accordingly. The process can then return to step 106, where the process of sensing soil variability and/or clod stability, calculating any necessary changes, updating motion of the implement, and determining whether a input is received, continues in a loop, while the implement traverses the field. However, if at decision step 112 a selection is not received ("No"), processor 45 can instead return to step 106, repeating the loop, without an update to any parameters.

It can be appreciated that the above description is merely exemplary of the present invention. Various modes of carrying out the invention are contemplated as being within the scope of the following claims particularly pointing out and distinctly claiming the subject matter, which is regarded as the invention.

What is claimed is:

1. A system for treatment of an agricultural field, comprising:
    a sensor for connecting to an agricultural implement, the sensor being an acoustic backscatter sensor array configured to transmit acoustic energy to the field and sense sound energy scattered back to the backscatter sensor array as the implement traverses the field and providing the sensed sound energy as a sensed signal; and
    a processor operatively connected to the sensor, the processor executing a program stored in non-transitory computer-readable storage medium to:
        estimate a clod size distribution of the soil in the field in response to the sensed sound energy; and
        change a speed of the implement in response to the estimated clod size distribution of the soil in the agricultural field; and
        change an application of a ground engaging tool of the agricultural implement in response to the estimated clod size distribution of the soil in the agricultural field.

2. The system of claim 1, wherein the processor executes to determine the estimated clod stability of soil in the field from an intensity of the sound energy scattered back.

3. The system of claim 1, wherein the agricultural implement is selected from one of a planter, a fertilizer applicator and a tillage implement.

4. The system of claim 1, further comprising a data structure containing a plurality of parameters, wherein the processor is operatively connected to the data structure, and further comprising the processor executing to compare the estimated clod size distribution of the soil in the agricultural field to a parameter of the data structure to cause the change.

5. The system of claim 4, wherein the change is an increase in speed of the implement in response to the estimated clod size in the field below a threshold, wherein the threshold is a parameter stored in the data structure.

6. The system of claim 4, wherein the change is a decrease in speed of the implement in response to the estimated clod size in the field above a threshold, wherein the threshold is a parameter stored in the data structure.

7. The system of claim 4, wherein the change is to the application of the seedbed attachment, the change comprising an increase in at least one of a pressure of a cylinder controlling a ground-engaging tool and a position of the ground-engaging tool to achieve a deeper ground engaging depth in response to the estimated clod size in the field above a threshold, wherein the threshold is a parameter stored in the data structure.

8. The system of claim 4, wherein the change is to the application of the seedbed attachment, the change comprising an decrease in at least one of a pressure of a cylinder controlling a ground-engaging tool and a position of the ground-engaging tool to achieve a shallower ground engaging depth in response to the estimated clod size in the field below a threshold, wherein the threshold is a parameter stored in the data structure.

9. The system of claim 4, further comprising a display in an operator cab associated with the agricultural implement, wherein the parameters are accessible through the display.

10. An agricultural implement comprising:
    a frame supported by a plurality of wheels;
    a ground engaging tool supported by the frame, wherein the ground engaging tool is configured to break soil in the field with adjustability to facilitate deposition of agricultural product at a desired depth;
    a sensor operatively connected to the implement, the sensor being an acoustic backscatter sensor array configured to transmit acoustic energy to the field and sense sound energy scattered back to the backscatter sensor array as the implement traverses the field and providing the sensed sound energy as a sensed signal; and a processor operatively connected to the sensor, the processor executing a program stored in non-transitory computer-readable storage medium to:
estimate a clod size distribution of the soil in the field in response to the sensed sound signal; and
cause a change to a speed of the implement in response to the estimated clod size distribution of the soil in the agricultural field; and
cause a change to an application of the ground engaging tool in response to the estimated clod size distribution of the soil in the agricultural field.

11. The implement of claim 10, wherein the processor executes to determine a magnitude of the estimated clod stability of soil in the field from an intensity of the sound energy scattered back.

12. The implement of claim 10, wherein the ground engaging tool comprises reels configured as crumblers having spirally arranged blades or bars with adjustability for reducing clod sizes.

13. A method for treatment of an agricultural field, comprising:
transmitting acoustic energy to the agricultural field with an acoustic backscatter sensor array operatively connected to an agricultural implement while the agricultural implement traverses the agricultural field;
sensing sound energy scattered back to the backscatter sensor array and providing the sensed sound energy as a sensed signal;
estimating a clod stability of soil in the agricultural field in response to the sensed signal;
and
processing a value in response to the estimated clod stability of soil in the agricultural field to change a speed of the implement and to change to an application of a ground engaging tool of the agricultural implement in response to the estimated clod size distribution of the soil in the agricultural field.

14. The method of claim 13, further comprising the step of determining a magnitude of the clod stability of soil in the agricultural field from an intensity of the sound energy scattered back.

15. The method of claim 13, further comprising changing the speed of the implement to increase the speed in response to the estimated clod size in the agricultural field below a threshold.

* * * * *